US00PP22355P3

(12) United States Plant Patent
Lowe

(10) Patent No.: US PP22,355 P3
(45) Date of Patent: Dec. 20, 2011

(54) KIWIFRUIT PLANT NAMED 'ZESY002'

(50) Latin Name: *Actinidia chinensis*
Varietal Denomination: ZESY002

(75) Inventor: Russell G. Lowe, Te Puke (NZ)

(73) Assignee: Zespri Group Limited, Mount Maunganui South (NZ)

( * ) Notice: Subject to any disclaimer, the term of this patent is extended or adjusted under 35 U.S.C. 154(b) by 0 days.

(21) Appl. No.: 12/660,397

(22) Filed: Feb. 24, 2010

(65) Prior Publication Data

US 2010/0333243 P1 Dec. 30, 2010

Related U.S. Application Data

(60) Provisional application No. 61/269,960, filed on Jun. 30, 2009.

(51) Int. Cl.
*A01H 5/00* (2006.01)

(52) U.S. Cl. ..... Plt./156

(58) Field of Classification Search ..... Plt./156
See application file for complete search history.

(56) References Cited

U.S. PATENT DOCUMENTS

PP11,066 P 9/1999 Lowe et al.

*Primary Examiner* — June Hwu
(74) *Attorney, Agent, or Firm* — Knobbe Martens Olson & Bear, LLP

(57) ABSTRACT

A new and distinct kiwifruit variety is disclosed. The variety results from selection among a population of seedlings derived from crossing the kiwifruit selections known as 51-18-15i.97 (not patented) and 51-18-20j.97 (not patented). The fruit of this new kiwifruit variety is characterized by large fruit size, high yield potential, ovoid shape, yellow flesh color, and early harvest maturity. The new kiwifruit variety has been named 'ZESY002'.

5 Drawing Sheets

Latin name of the genus and species of the plant claimed: *Actinidia chinensis.*

Variety denomination: 'ZESY002'.

BACKGROUND AND SUMMARY OF THE INVENTION

The invention relates to the discovery and asexual propagation of a new and distinct variety of kiwifruit, *Actinidia chinensis* 'ZESY002', as herein described and illustrated. The new kiwifruit variety 'ZESY002' was selected from a population of seedlings derived from crossing two kiwifruit selections 51-18-15i.97 (maternal; not patented) and 51-18-20j.97 (paternal; not patented) in the course of a planned kiwifruit variety breeding program. The cross was made in November 2000 at Te Puke, Bay of Plenty, New Zealand. The new variety was selected as 13-15-14g.02 and has been named 'ZESY002'.

The new kiwifruit variety 'ZESY002' may be distinguished from presently available *Actinidia* cultivars by the following distinguishing characteristics:

The fruit of the new kiwifruit variety 'ZESY002' mature earlier than those of 'Hort16A' (U.S. Plant Pat. No. 11,066).

'ZESY002' produce much larger fruit than those of 'Hort16A' and also produce more flowers.

The fruit shape at the stylar end of the new variety 'ZESY002' is blunt with a slight indentation compared with that of 'Hort16A', which extends into a characteristic 'beak'.

The flesh of the new kiwifruit variety 'ZESY002' fruit is yellow in color (similar to 'Hort16A') when ripe for consumption, compared with 'Hayward', which is green in color.

'ZESY002' is tetraploid compared with 'Hort16A', which is diploid.

'ZESY002' is distinguished from its maternal parent (51-18-15i.97) by characteristics including the time of harvest; 'ZESY002' requires approximately six weeks longer to accumulate 10% soluble solids.

'ZESY002' is distinguished from its paternal parent (51-18-20j.97) as it is a female fruit bearing kiwifruit variety whereas 51-18-20j.97 is a male non-fruit baring kiwifruit.

Asexual propagation of the new kiwifruit variety 'ZESY002', in Te Puke, Bay of Plenty, New Zealand, by grafting shows that the unique combination of characteristics of the variety come true to form and are established and transmitted through succeeding propagation. In order to obtain true-to-type clones of the initial plant, asexually propagated plants were obtained by grafting dormant buds from the original seedling onto rootstocks.

BRIEF DESCRIPTION OF THE DRAWINGS

The accompanying photographs show typical specimens in full color of the fruit, flowers, and leaves of the new variety 'ZESY002', plants observed were three years old. The colors as depicted are as nearly true as is reasonably possible in a color representation of this type.

DETAILED DESCRIPTION OF THE PREFERRED EMBODIMENT

The following is a detailed description of the new variety. The specimens described were grown at Te Puke, Bay of Plenty, New Zealand. The observations were made on vines grafted onto existing *A. deliciosa* seedling rootstock, and managed under standard orchard practice. This included growing the plants on a standard pergola structure at a height of 1.8 m, and each plant was allowed to occupy a canopy area of approximately 15 $m^2$. The plants were three years old when described, and considered mature. Random measurements of each characteristic were obtained from samples of 6 plants.

Horticultural terminology is used in accordance with UPOV guidelines for kiwi. All dimensions are in millimeters, and all weights are in grams (unless otherwise stated). Certain characteristics of this variety, such as growth and color, may change with changing environmental conditions (e.g., light, temperature, moisture), nutrient availability, rootstocks, or other factors. Color descriptions and other terminology are used in accordance with their ordinary dictionary descriptions, unless the context clearly indicates otherwise. Color names beginning with a capital letter designate values based upon The R.H.S. Colour Chart 2001 edition published by The Royal Horticultural Society, London, England.

Plant and Foliage

The plant is a female plant that is tetraploid and expresses a twining habit of medium to strong vigor, producing many long thick one-year-old canes and large leaves.

Tomentose hairs are present on the young shoot at low density. Anthocyanin (red) coloration of the growing tip is absent or very weak on most shoots.

The mature one-year-old shoots of the plant are smooth and colored light yellowish-brown (R.H.S.164B) on the upper side. There are a many large lenticels (1.75 mm average diameter), which are orange-brown in color (R.H.S. 165B), raised in appearance, and elliptical in shape. The size of the bud support is small and the leaf scar is moderate in size (similar to 'Hort16A'). Mature one-year-old shoots are thick, averaging 14.6 mm in diameter between bud 5 and 6.

Figure 7:
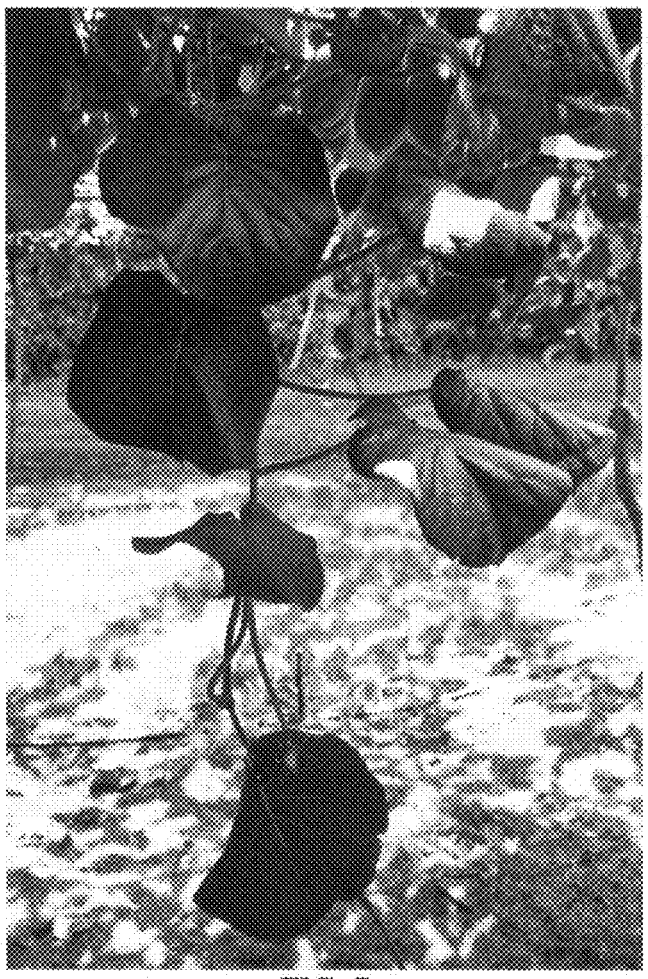
FIG. 7 shows mature leaves of the new kiwifruit variety 'ZESY002' (on the vine).
Figure 8:
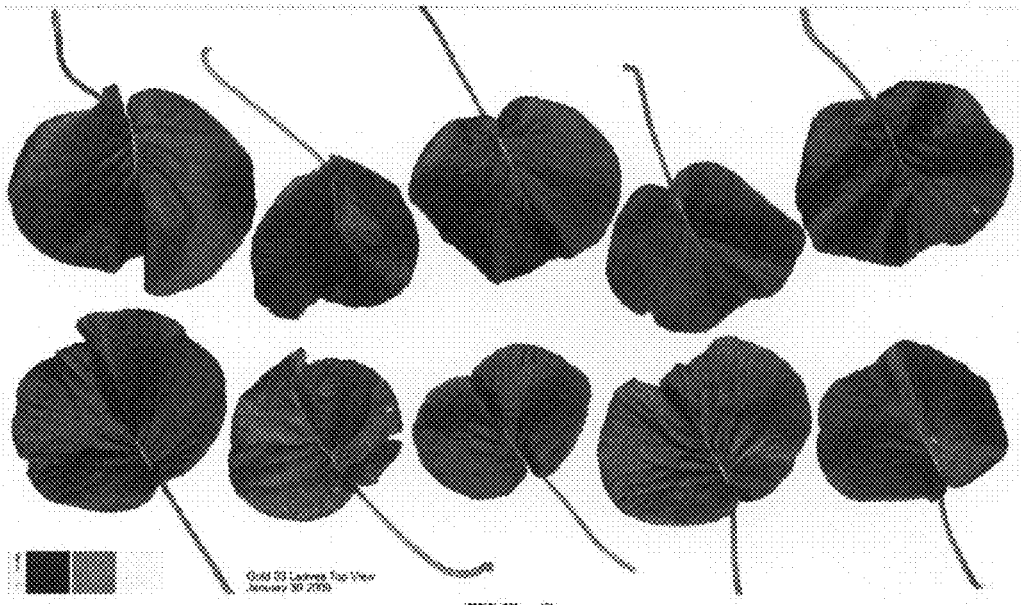
FIG. 8 shows mature leaves of the new kiwifruit variety 'ZESY002' from above (adaxial surface) (in the studio).
Figure 9:
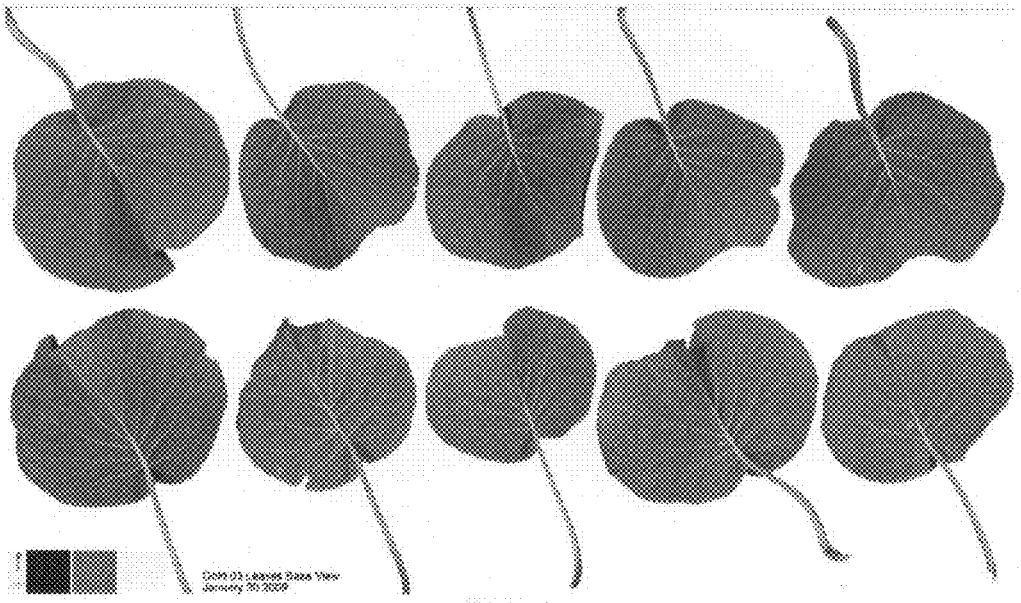
FIG. 9 shows mature leaves of the new kiwifruit variety 'ZESY002' from below (abaxial surface) (in the studio).

The leaf of 'ZESY002' is cordate in shape with an emarginate shaped leaf tip (FIG. 7, FIG. 8, FIG. 9) and typically averages approximately 167 mm in length and 209 mm in width, the texture of a mature leaf is considered to be moderately rough. The leaf bases are slightly touching. The color of the leaf blade is moderate green (R.H.S. 139B) on the upper surface and greenish-yellow (R.H.S.147B) on the lower surface; with no variegation observed. Leaf petioles are approximately 162 mm long and 6 mm thick on average and have weak anthocyanin coloration on the upper side of the petiole (R.H.S. 60A or 181A). Petioles have a sparse covering of short, soft hairs; while on the underside of the leaves there is a dense covering of hairs on the veins, no spines have been observed on these leaves.

Inflorescence

The number of flowers in each inflorescence is typically between one to three flowers, with each inflorescence comprising a single king flower that produce the largest fruit and up to two side flowers (0.4 per inflorescence on average) that produce smaller fruit. Each fruiting one-year-old shoot, typically develops between one and nine inflorescences, with an average of 5.2.

Flower pedicels average approximately 38 mm in length at mid-bloom.

Figure 6:
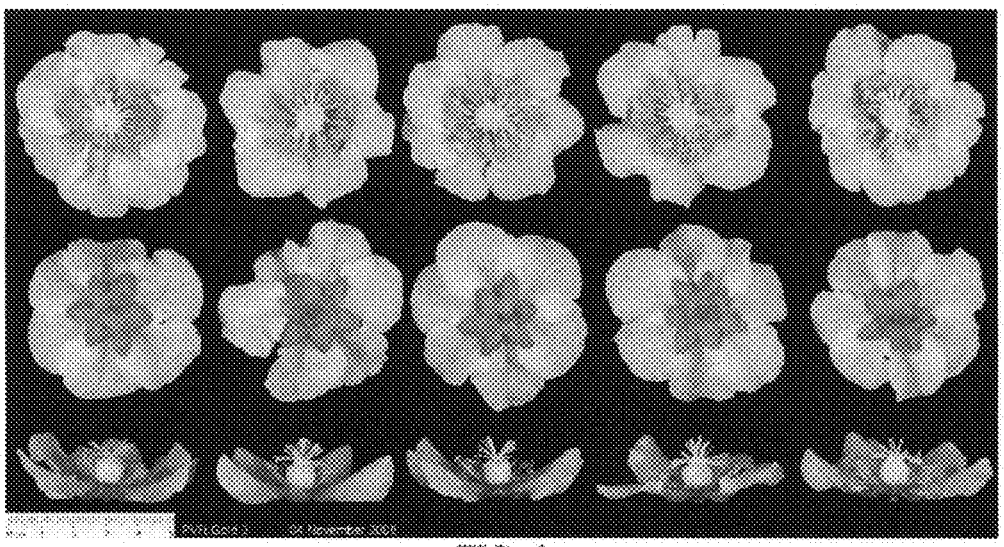
FIG. 6 shows the flowers of the new kiwifruit variety 'ZESY002' (in the studio).

There are between five and nine petals on each flower, with an average of 6.9. The petals are arranged overlapping and are white in color (R.H.S. 158B) when fully open, but with a light green base (R.H.S. 146C) (FIG. 6). Petals are involute in shape in cross-section and there is a mixture of smooth and crimped petal shapes giving the appearance of an irregular or 'untidy' flower. Flowers also contain between six and seven sepals (6.9 on average) that are mainly green in color (R.H.S. 143C), but with a distinct yellow-brown color (R.H.S. 164B) around the edges (FIG. 6). A 2 mm wide calyx ring is present. Each flower produces between 28 and 37 styles (32 on average) with a semi-erect attitude that are 6.1 mm long on average and white in color (R.H.S. 155D). There are an average of approximately 59 stamens per flowers with yellow anthers (R.H.S. 15A).

Ovaries of the king flower are covered in fine hairs that are white in color (R.H.S. 155D). Anthocyanin (red) coloration of the ovaries in cross-section is absent at mid-bloom. Ovaries of the king flower have a mean length of 10.1 mm and are ovoid in shape.

Fruit

Figure 3:
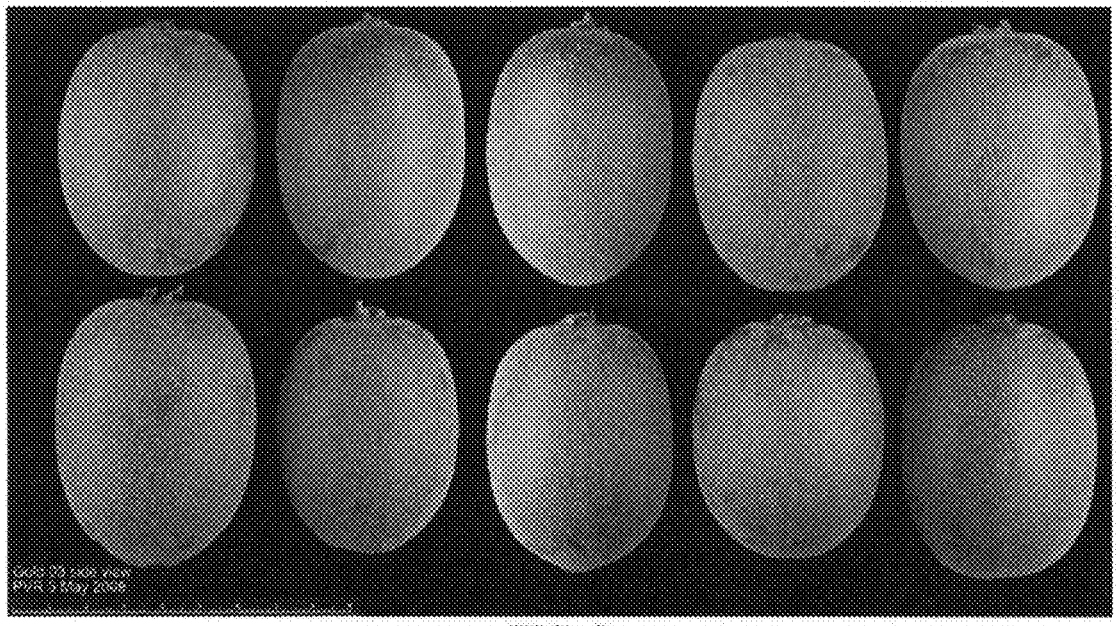
FIG. 3 shows typical fruit of the new kiwifruit variety 'ZESY002' (in the studio).
Figure 4:
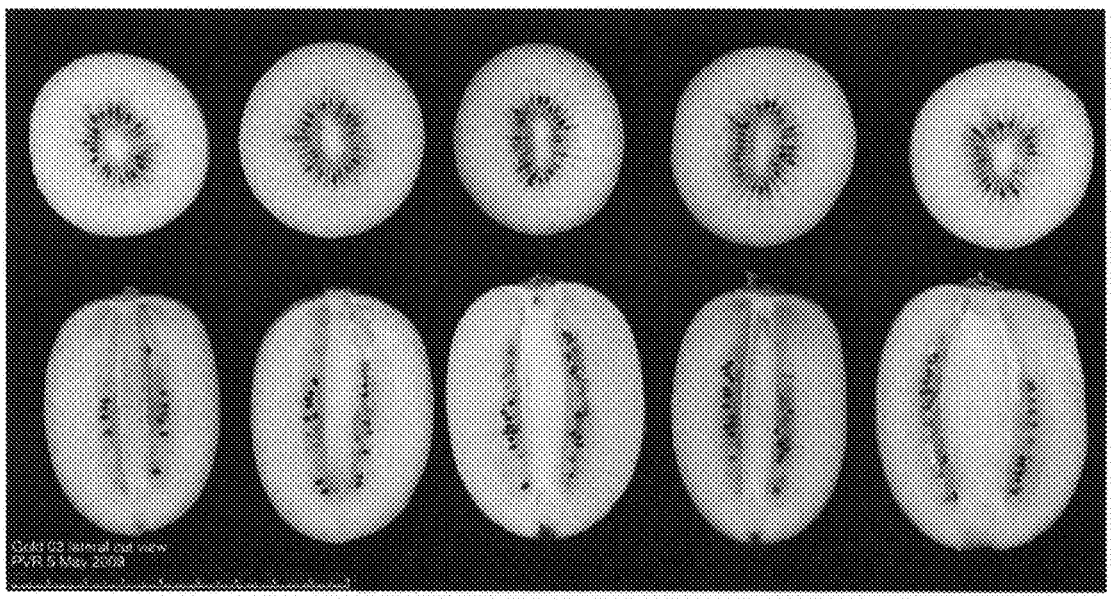
FIG. 4 shows the fruit of the new kiwifruit variety 'ZESY002' in longitudinal-section and cross-section (in the studio).

'ZESY002' fruit are large in size, approximately 136 g in weight on average when thinned to a crop load of approximately 46 fruit per square meter of female canopy. The fruit dimensions average 73.4 mm in length, 54.8 mm maximum width, and 51.1 mm minimum width. The general fruit shape in longitudinal section is ovoid, with the general shape of the stylar end being flat with a slight dent (FIG. 3, FIG. 4) and the general shape at the stalk end being rounded. In cross-section, fruit shape at the median part of the fruit varies circular to partially elliptic, with most fruit being at least partially elliptic in shape (FIG. 4).

Fruit stalks are of medium length, averaging 46 mm long and 3.6 mm in diameter and are brown in color (R.H.S. 199C and 200C).

Soft light brown (R.H.S. 165B) hairs are present on the mature fruit, but hairs are very short and occur at very low density. The skin of fruit is yellow-green in color (R.H.S. 148B) when fruit have been protected from direct sun exposure, but the skin changes to dark brown in color (R.H.S. 200D) on exposed fruit. The skin is covered with numerous lenticels that are light orange white in color (R.H.S. 164C) and are quite conspicuous. The combination of lenticels and underlying skin colors give the fruit an overall appearance of a light brown color (199B) when viewed from a distance of 30 cm or more.

The outer pericarp is initially a light green color (R.H.S. 164C) during early fruit development. The outer pericarp then gradually changes to a light yellow color (R.H.S. 8D) over a six to eight week period as fruit mature during February and March, reaching a yellow flesh hue angle of 103° by approximately April 1 in the Te Puke region of New Zealand. A ring of slightly greener colored tissue (R.H.S. 143C or 143D) immediately under the skin can persist in some fruit, particularly if they have been exposed to direct sunlight during development. The inner pericarp is light yellow in color (R.H.S. 8C) at maturity for consumption (FIG. 4). The core of the mature fruit is yellowish-white (R.H.S. 9D or 8D), ovoid or elliptic in shape, and is approximately 10.2 mm in average diameter. Each fruit contains between 27 and 37 locules (31 on overage) and between 13 and 32 seeds can be counted on a transverse slice made through the middle of the fruit (24 on average).

Fruit flavor is very sweet and mild with a tangy after taste and a characteristically smooth texture. Fruit can be ripened soon after they have been harvested in late March or early April in the Te Puke region of New Zealand using ethylene gas, or will soften during cold storage and become ripe for eating within 18 to 24 weeks at 1° C. The fruit average 17.4% soluble solids (measured as ° Brix) and contain 117 mg of vitamin C and 1.10 g of titratable acidity (g citric acid equivalents) per 100 g of fresh weight at maturity for consumption.

Cultivation

'ZESY002' plants can be grown on the same rootstocks as other standard varieties such as 'Hayward' and 'Hort16A'. Rootstocks currently being used in New Zealand include *A. deliciosa* seedlings, *A. chinenis* seedlings, and 'Kaimai' (not patented).

Figure 5:
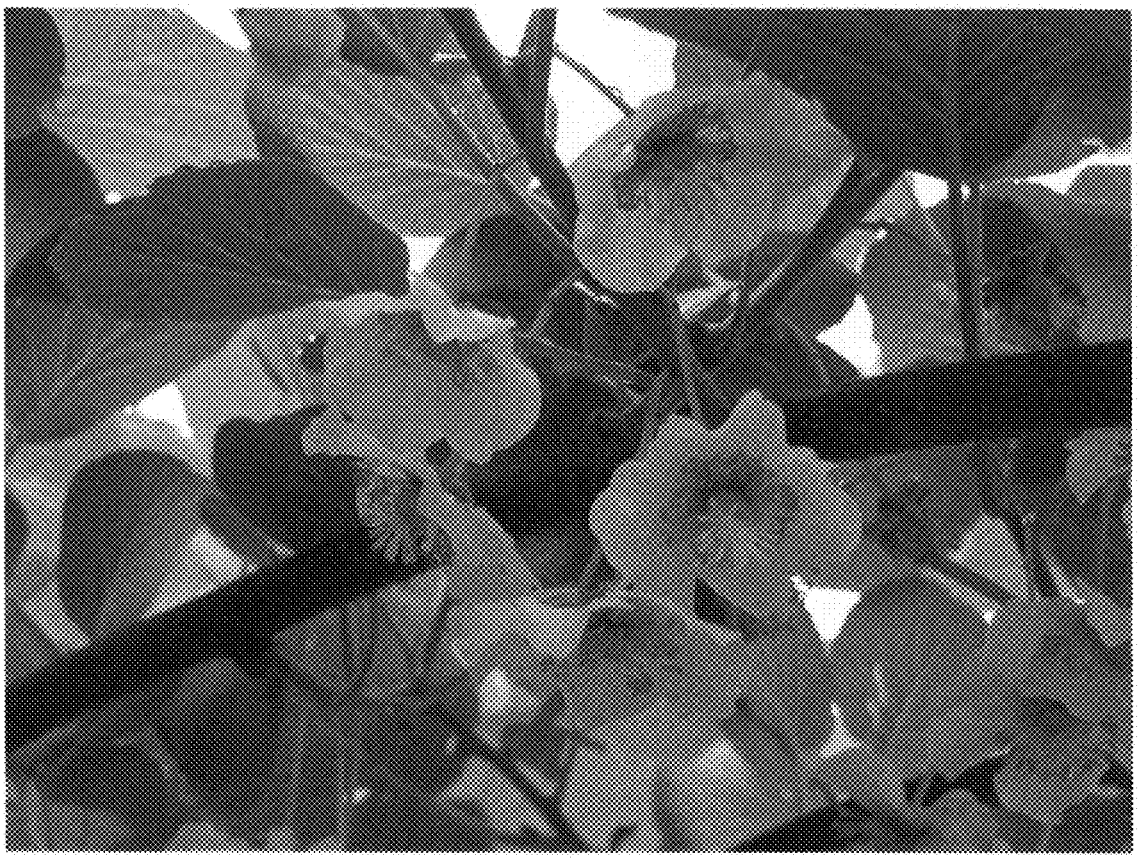
FIG. 5 shows the flowers of the new kiwifruit variety 'ZESY002' (on the vine).

Vegetative bud break occurs in early September in the Te Puke region of New Zealand, with flowering commencing in late October, with a flowering period of approximately 14 days (FIG. 5). In the Te Puke region of New Zealand, more than ⅔ of the dormant 'winter' buds burst in spring and approximately 94% of these shoots will produce flowers. All flowers produced appear capable of setting a fruit that will survive to harvest, if they are pollinated. The fruit attain maturity for harvest according to the criteria of reaching 103° hue angle of the outer pericarp in early April in the Te Puke region of New Zealand. However, harvest of the fruit can be conducted earlier than this if the fruit are held at temperatures of 10° C. for up to one month, to allow the yellow flesh color to develop. Leaves persist on the plants until early winter (June to July) in the Te Puke region of New Zealand.

Figure 1:
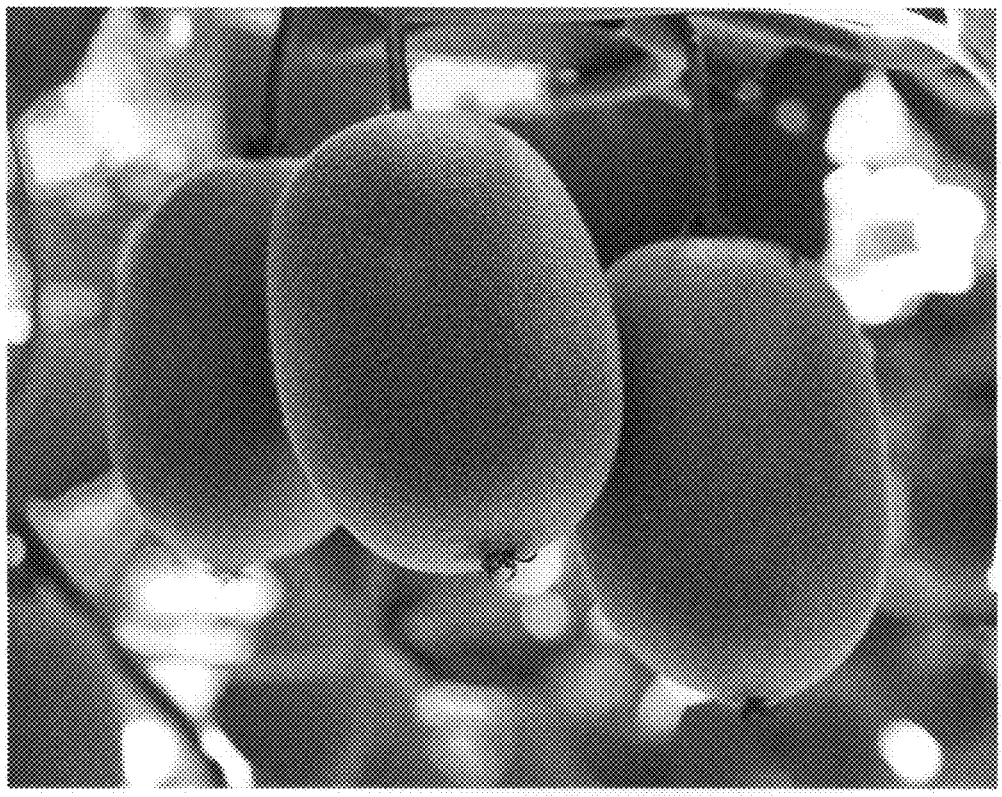
FIG. 1 shows typical fruit of the new kiwifruit variety 'ZESY002' (on the vine).
Figure 2:
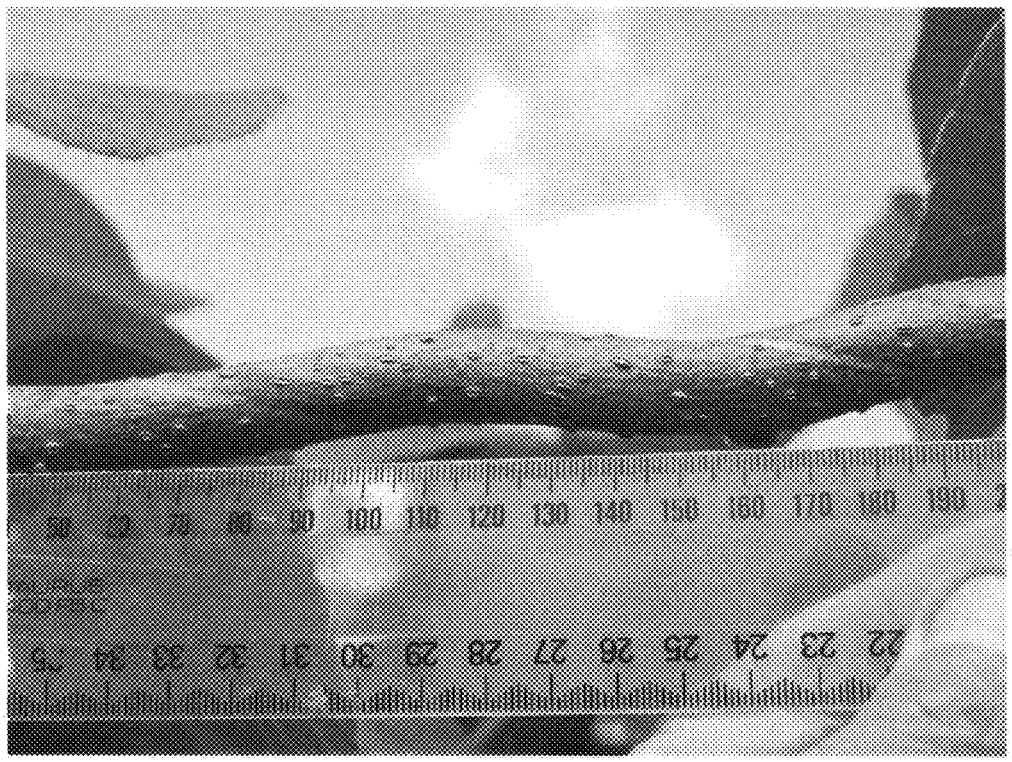
FIG. 2 shows typical one-year-old shoots (canes) of the new kiwifruit variety 'ZESY002' (on the vine).

In the absence of budbreak enhancing chemicals, plants produce moderate to high flower numbers, with an average of 30 to 40 king flowers per meter of one-year-old cane in the Te Puke region of New Zealand. In non-thinned vines this would result in crop loads of 90 to 120 fruit per square meter of female canopy at standard cane spacings (FIG. 1). Due additionally to the large average fruit size that are produced by 'ZESY002', 'ZESY002' potentially have a high natural yield potential relative to other cultivars of kiwifruit currently being grown. Fruit size is large (136 g) when thinned to a crop load of approximately 46 fruit per square meter of female canopy. The large natural fruit size of 'ZESY002' means that it has the potential to deliver high natural yields in environments where crop loads of 30-50 fruit per square meter can be maintained relative to other cultivars of kiwifruit currently being grown.

Dormant canes of 'ZESY002' appear to be susceptible to Latania scale (*Hemiberlesia lataniae*) and leaves appear to be susceptible to brown headed leafroller (*Ctenopseustis obliquana*). There is also some evidence to suggest that fruitlets may have an increased susceptibility to *Sclerotinia sclerotiorum* infection when compared with 'Hort16A'. No other host susceptibility testing has been completed at this stage.

Observations to date suggest that 'ZESY002' plants have a similar plant hardiness zone to 'Hort16A' plants.

In post harvest storage, softening of harvested 'ZESY002' fruit can be delayed by placing fruit into cold storage. In this case, fruit can be successfully stored for between 12 and 24 weeks while maintaining average flesh firmness greater than one kgf. Once removed from cold store and returned to ambient temperatures, the fruit continue to soften but can be held at 20° C. for one to two weeks for consumption.

I claim:

1. A new and distinct kiwifruit plant substantially as herein described and illustrated, characterized by fruit having a large size, high natural yield potential, ovoid shape, yellow flesh color, and early harvest maturity.

* * * * *